(12) United States Patent
Cohen

(10) Patent No.: US 9,410,960 B2
(45) Date of Patent: Aug. 9, 2016

(54) METHOD OF DIAGNOSING GALACTOSEMIA IN NEONATAL SCREENING

(71) Applicant: Statens Serum Institut, Copenhagen S (DK)

(72) Inventor: Arieh Sierra Cohen, Lund (SE)

(73) Assignee: Statens Serum Institut, Copenhagen (DK)

( * ) Notice: Subject to any disclaimer, the term of this patent is extended or adjusted under 35 U.S.C. 154(b) by 0 days.

(21) Appl. No.: 14/443,997

(22) PCT Filed: Nov. 28, 2013

(86) PCT No.: PCT/DK2013/000084
§ 371 (c)(1),
(2) Date: May 19, 2015

(87) PCT Pub. No.: WO2014/086361
PCT Pub. Date: Jun. 12, 2014

(65) Prior Publication Data
US 2015/0293111 A1     Oct. 15, 2015

(30) Foreign Application Priority Data
Dec. 3, 2012 (DK) .................... 2012 00767

(51) Int. Cl.
*C12Q 1/00* (2006.01)
*G01N 33/66* (2006.01)
*C12Q 1/54* (2006.01)
*C12Q 1/68* (2006.01)

(52) U.S. Cl.
CPC *G01N 33/66* (2013.01); *C12Q 1/00* (2013.01); *C12Q 1/54* (2013.01); *C12Q 1/6827* (2013.01); *C12Q 1/6883* (2013.01); *G01N 2400/00* (2013.01); *G01N 2800/042* (2013.01); *G01N 2800/385* (2013.01); *G01N 2800/50* (2013.01)

(58) Field of Classification Search
CPC ...... C12Q 1/6827; C12Q 1/6883; C12Q 1/00; C12Q 1/54; G01N 2800/50
See application file for complete search history.

(56) References Cited

U.S. PATENT DOCUMENTS

| 6,451,611 | B1* | 9/2002 | Simonsen | G01N 33/66 435/105 |
| 6,913,879 | B1* | 7/2005 | Schena | C12Q 1/6827 435/287.2 |
| 2003/0228704 | A1* | 12/2003 | Dooley | G01N 33/64 436/173 |
| 2008/0274563 | A1* | 11/2008 | Cerda | G01N 33/64 436/173 |

OTHER PUBLICATIONS

Jensen et al, "Neonatal Screening for Galactosemia by Quantitative Analysis of Hemose Monophosphateses Using Tandem Mass Spectrometry: A Retrospective Study", Clinical Chemistry 47:8, 2001 (pp. 1364-1372).*

(Continued)

*Primary Examiner* — Jennifer Wecker
(74) *Attorney, Agent, or Firm* — Howson & Howson LLP

(57) ABSTRACT

A method of diagnosing galactosemia in blood samples from neonates by determining GAL-1-P concentrations before 5-7 days of life is disclosed. The removal of interfering compounds allows a more specific and therefore more accurate determination of GAL-IP levels in newborn screening for galactosemia using mass spectrometry. This is of major importance when investigating samples from children that have not yet achieved a steady state of GAL-IP (i.e. before 5-7 day of life).

20 Claims, 2 Drawing Sheets

(56) References Cited

OTHER PUBLICATIONS

Figure 1:
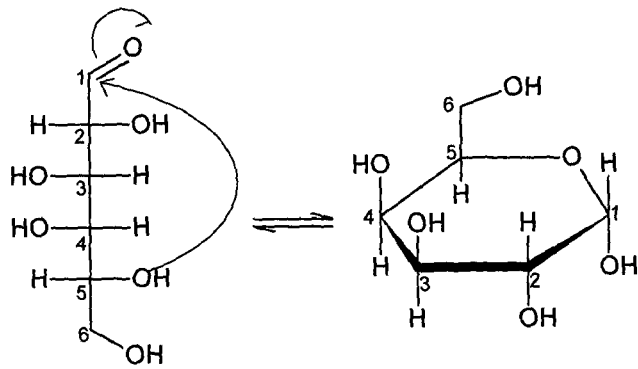

Jensen, et al., Neonatal screening for galactosemia by quantitative analysis of hexose monophosphates using tandem mass spectrometry: a retrospective study, Clinical Chemistry, Aug. 2001, 47(8): 1364-1372.

Turgeon, et al., Combined newborn screening for succinylacetone, amino acids, and acylcarnitines in dried blood spots, Clinical Chemistry, e-pub Feb. 15, 2008, 54(4): 657-664.

* cited by examiner

METHOD OF DIAGNOSING GALACTOSEMIA IN NEONATAL SCREENING

FIELD OF INVENTION

The invention discloses a method of diagnosing galactosemia by determining GAL-1-P concentrations in blood samples from neonates taken before 5-7 days of life.

GENERAL BACKGROUND

Galactosemia is a life threatening inborn error of metabolism. It is caused by a deficiency in the enzyme galactose-1-phosphate uridyl transferase (GALT). GALT is important in the metabolism of galactose and it catalyses an important step in the conversion of galactose-1-phosphate (GAL-1-P) to glucose-6-phosphate (GLC-6-P). In patients with galactosemia the conversion is very low or non-existing leading to harmful levels of GAL-1-P and metabolites thereof.

In many countries galactosemia screening is part of the national newborn screening programmes. At present, an enzyme activity test (i.e. Beutler test) is the predominant method used for galactosemia screening (Beutler E, Baluda M C. A simple spot screening test for galactosemia. J Lab Clin Med 1966; 68:137-141). The main advantage to the Beutler test is that it measures enzyme activity rather than metabolite concentrations. The main disadvantage is that it requires the enzyme activity to be intact. Enzymes are sensitive to heat and can be rendered inactive by excessive heat thus leading to false positives. Also, the Beutler test calls for a sample of its own. It is not possible to multiplex it with other screening tests.

It is also possible use metabolites as biomarkers when screening for galactosemia. Biomarker based screening for galactosemia using mass spectrometry has previously been described in WO0210740. Briefly, elevated levels of hexose-monophosates are used as biomarkers for the disease. This is based on the fact that galactosemia leads to elevated levels of GAL-1-P, which is a hexose-monophosphate. Ideally, screening should be based on GAL-1-P alone. However, in mass spectrometry (MS) it is not possible to differentiate between different types of hexose-monophosphates. It is possible to use liquid chromatography prior to mass spectral determination (LC-MS) in order to differentiate between them but this is not practicable in newborn screening due to the demands of high sample throughput. The rational for using total hexose-monophosphate as a biomarker is that in patients with galactosemia GAL-1-P levels becomes elevated above the levels of all other hexose-monophosphates. An abnormal concentration of total hexose-monophosphates is definitely indicative of galactosemia. This approach is effective in detecting patients who are receiving galactose containing food. Breast milk, cow milk and milk based foods contain lactose which consists of a galactose and a glucose unit joined by a 1,1-glucoside bond. It is quickly converted to galactose and glucose in the digestive tract. Neonates on a normal diet are therefore exposed to high levels of galactose and if they have galactosemia their levels of GAL-1-P will increase dramatically.

However, at birth several types of hexose-monophosphates are present at low levels in neonates, predominantly GLC-6-P. The presence of GLC-6-P causes a background level in the measurement of total hexose-monophosphates which in turn has a detrimental effect on the specificity and sensitivity of the screening method. For the hexose-monophosphate method to function properly the levels of GAL-1-P have to be substantially above the levels of GLC-6-P in order to be able to detect a positive sample. Although the levels of GAL-1-P are elevated at birth in patients with galactosemia the levels only rise dramatically after several days of ingesting food containing galactose. Typically a steady state is obtained after 3 to 5 days after birth. The fact that it is necessary for the child to have ingested a significant amount of galactose prior to sampling is a major drawback in screening. In many countries newborn screening samples are taken before 3 to 5 days, also some newborns have feeding problems and reach steady state levels at a later time.

As mentioned earlier, GAL-1-P levels are elevated in galactosemia patients already at birth. If the background created by the presence of GLC-6-P could be removed it would be possible to screen for galactosemia in newborns. The present invention provides a mean to chemically deplete GLC-6-P without affecting GAL-1-P thereby making it possible to screening for galactosemia using mass spectrometric measurement of GAL-1-P independent of sampling time. A further advantage is that newborn screening with MS allows for multiplexing, i.e. it is possible to combine several screening test in one sample.

SUMMARY OF THE INVENTION

The present invention makes the analysis of GAL-1-P levels more specific. The removal of interfering compounds allows a more specific and therefore more accurate determination of GAL-1P levels in newborn screening for galactosemia using mass spectrometry. This is of major importance when investigating samples from children that have not yet achieved a steady state of GAL-1P (i.e. before 5-7 day of life).

DETAILED DISCLOSURE OF THE INVENTION

The invention discloses a method of determining GAL-1-P concentrations in an early blood sample from neonates by modifying the carbonyl groups of hexosemonophosphates. The modification of the carbonyl group is done by oxidation, reduction or reaction with an amine.

The reduction of the carbonyl group is preferably achieved by adding sodium borohydrate to the sample and the oxidation of the carbonyl group is preferably achieved by reacting the sample with nitric acid, or Tollen's or Fehling's agent. The carbonyl group is preferably modified by reacting the hexosemonophosphates in the sample with a hydrazine. Hydrazine is chosen from $N_2H_4$, monomethyl hydrazine, 1,1-dimethylhydrazine, 1,2-dimethylhydrazine, Isoniazid, iproniazid, hydralazine, phenelzine, 2,4-dinitrophenylhydrazine or phenylhydrazine, The samples from the neonatals are usually collected 3-5 days after birth but according to the present method samples can be collected just after the birth. The GAL-1-P concentration in the blood sample is preferably measured by mass-spectrometry The invention is based on the chemical depletion of all sugars that are not modified in the 1 position. Simple sugars are in equilibrium between a straight and a ring form. This equilibrium is based on a process known as anomerization in which the 5 position hydroxyl group forms a bond with the 1 position the sugar creating an oxygen bridge between the position of the keto group and the 1 position (FIG. 1). The aldehyde group subsequently forms a hydroxyl group. In the straight form the sugars are far more reactive as the oxygen of the keto group is much more reactive than the other oxygens of the carbohydrate as they are present as hydroxyl groups. When a functional group is added to a sugar in the 1 position (modified in the 1 position) it is no longer possible for it to convert to the straight form and it is locked in the ring form. When a sugar is locked in the ring form it no longer has the keto reactivity.

In the invention a reagent that primarily reacts with aldehydes and ketones but not with hydroxyl groups is allowed to react with the sample prior to analysis. All sugars that are not modified in the 1 position will react and form other compounds.

This allows for the depletion of GLC-6-P without affecting the levels of GAL-1-P. This means that GLC-6-P no longer will be present in the sample after the reaction. Thus only 1-modified hexose-monophosphates will contribute to the measurement of total hexose-monophosphates. The invention utilizes the fact that the carbonyl (i.e. aldehyde or keto group) group in sugars that are modified in 1 position are protected from chemical reactions. The chemical reaction used targets the carbonyl group without affecting the oxygens in the hydroxyl groups. There are a number of well-known chemical reactions that can be utilized. They generally fall into the following classes: reduction or oxidation of the carbonyl group or reactions with amines which will be well known for the skilled person.

Reduction of the carbonyl group, e.g. Sodium Borohydrate reduction. NaBH4 will reduce many organic carbonyls, converting ketones and aldehydes to alcohols. The metal hydride reductions and organometallic additions to aldehydes and ketones, both decrease the carbonyl carbon's oxidation state, and may be classified as reductions. As noted, they proceed by attack of a strong nucleophilic species at the electrophilic carbon. Other useful reductions of carbonyl compounds, either to alcohols or to hydrocarbons, may take place by different mechanisms. For example, hydrogenation (Pt, Pd, Ni or Ru catalysts), reaction with diborane, and reduction by lithium, sodium or potassium in hydroxylic or amine solvents have all been reported to convert carbonyl compounds into alcohols. However, the complex metal hydrides are generally preferred for such transformations because they give cleaner products in high yield.

Oxidation of the carbonyl group, e.g. Nitric acid, Tollens' or Fehling's reagent. The carbon atom of a carbonyl group has a relatively high oxidation state. This is reflected in the fact that most of the reactions described thus far either cause no change in the oxidation state (e.g. acetal and imine formation) or effect a reduction (e.g. organometallic additions and deoxygenations). The most common and characteristic oxidation reaction is the conversion of aldehydes to carboxylic acids. Preferred oxidizing agents are Ag(+) and Cu(2+) as oxidants.

Reactions with amines, e.g. Schiff base formation or reactions with hydrazine. The reaction of aldehydes and ketones with ammonia or 1°-amines forms imine derivatives, also known as Schiff bases, (compounds having a C=N function). A preferred amine for modifying the 1 position of the carbonyl (i.e. aldehyde or keto group) group in sugars is hydrazine ($N_2H_4$) but any hydrazine derivative can be used: Many substituted hydrazines are known, and several occur naturally. Some examples include monomethyl hydrazine, where one of the hydrogen atoms on the hydrazine molecule has been replaced with a methyl group (CH3). By the symmetry of the hydrazine molecule, it does not matter which hydrogen atom is replaced.

1,1-dimethylhydrazine (unsymmetrical dimethylhydrazine, UDMH) and 1,2-dimethylhydrazine (symmetrical dimethylhydrazine) are hydrazines where two hydrogen atoms are replaced by methyl groups.

Isoniazid, iproniazid, hydralazine, and phenelzine are compounds whose molecules contain hydrazine-like structures.

2,4-dinitrophenylhydrazine (2,4-DNPH) is commonly used to test for ketones and aldehydes in organic and clinical chemistry.

phenylhydrazine, C6H5NHNH2, the first hydrazine to be discovered.

These reactions produce compounds with a different molecular mass and can therefore easily be differentiated by mass spectrometry. This makes it possible to determine elevated levels of GAL-1-P independent of galactose exposure. Tandem mass spectrometry is extensively used in newborn screening due to the fact that a wide range of compounds can be analysed concurrently in a single sample. This makes it possible to screen for a number of diseases in a single analysis. Any chemical reaction that is introduced to the screening should preferably not interfere with the analysis of other analytes. In order to achieve this we have chosen to use hydrazine although any carbonyl specific reagent could be used to improve galactosemia screening on its own.

In newborn screening, hydrazine is widely used to make it possible to screen for tyrosinemia. In this case hydrazine is used to release protein bound succinyl acetone so that it can be determined by mass spectrometry. The reason for this approach is that in tyrosinemia an excess of succinyl acetone is produced. Elevated blood levels of succinyl acetone would be an attractive biomarker of tyrosinemia, however succenyl acetone reacts rapidly with proteins which are present in high amounts in blood. Succinyl acetone forms covalent bonds with proteins. Hydrazine reacts in such as fashion as to break the bond with the protein thus releasing succinyl acetone. In this manner succinyl acetone can be used as a biomarker despite its reactivity towards proteins. This use of hydrazine is fundamentally differently than the one we utilize in galactosemia screening. We use hydrazine to lower the levels of interfering compounds whereas the function of hydrazine in tyrosinemia screening is to increase the level of the biomarker.

Hydrazine is known to not interfere with other biomarkers that are utilized in newborn screening. Thus hydrazine is an attractive reagent for galactosemia screening as it improves the sensitivity and selectivity of the method while not interfering with other newborn screening analytes.

In tandem mass spectrometry analytes are first selected according to their mass to charge ratio. They are subsequently fragmented and specific fragments are detected. The combinations of mass to charge ratio and fragment mass is known as a transition. Using transitions allows for specific determination of compounds based on two chemical properties, molecular mass and fragmentation pattern. Since all hexose monophosphates have the same mass and fragment in the same manner it is not possible to differentiate between different hexosemonophosphates (HMP) by mass spectrometry alone. Using on line liquid chromatography it is possible to separate the HMPs prior to mass spectrometry. In this manner it is possible to differentiate between various HMPs. However, this is time consuming and is not practicable in newborn screening. Chemically depleting all HMPs that are not modified in the 1 position (most importantly GLC-6P) increases the specificity of the method without the need for chromatography.

The invention makes it possible to screen for galactosemia by mass spectrometry using the metabolite GAL-1-P as a biomarker of the disease regardless of the level of exposure to galactose. In patients with galactosemia GAL-1-P levels are elevated. However, it is only after exposure to galactose that the levels of GAL-1-P raise well above the levels of GLC-6-P. All HMPs have the same mass and fragment in the same manner (i.e. have the same transitions). Therefore GLC-6P provides a background that masks the mild elevation present before exposure to galactose. The main source of galactose is lactose, which is present in high concentrations in milk and milk products. Lactose is quickly converted to glucose and galactose when ingested. Galactosemia patients generally reach a steady state of GAL-1P after three to five days of exposure to galactose. Thus, unless GLC-6P is not removed from the sample mass spectrometry screening for galactosemia using GAL-1P is only feasible using samples taken after 5 days. Many screening programs take the sample before this time. Also, children that have not been exposed to galactose (e.g. fed by glucose drip, allergic to milk) cannot be screened.

By adding a reagent that reacts will all HMPs that are not modified in the 1 position the background signal caused by other HMPs is removed. The chemical reaction causes a change in the mass of the compounds and also changes how they fragment. This means that they will no longer provide a signal in the transition used for HMPs. This makes it possible to screen for galactosemia irrespective of galactose exposure and therefore sample time.

FIGURE LEGENDS

Figure 2:
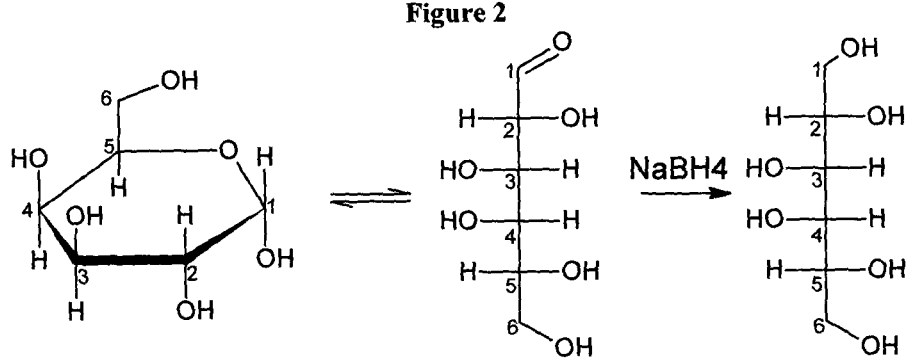
Figure 3:
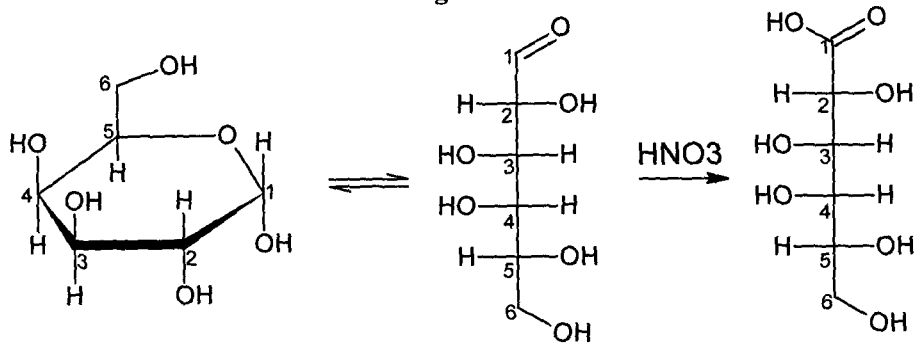
Figure 4:
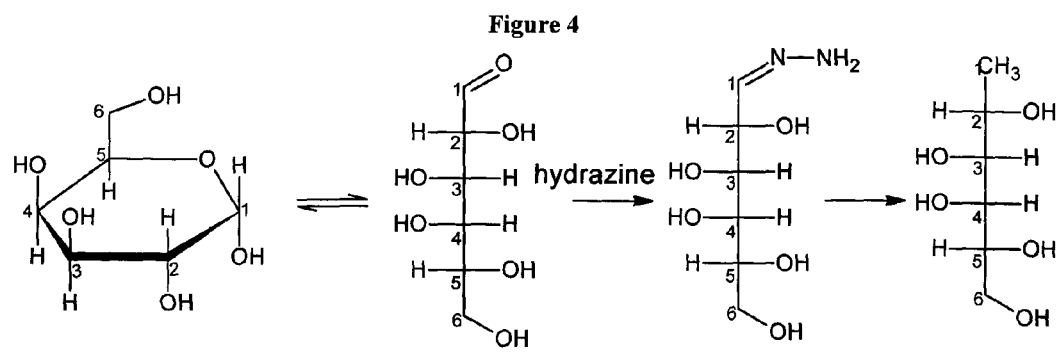
Figure 4:
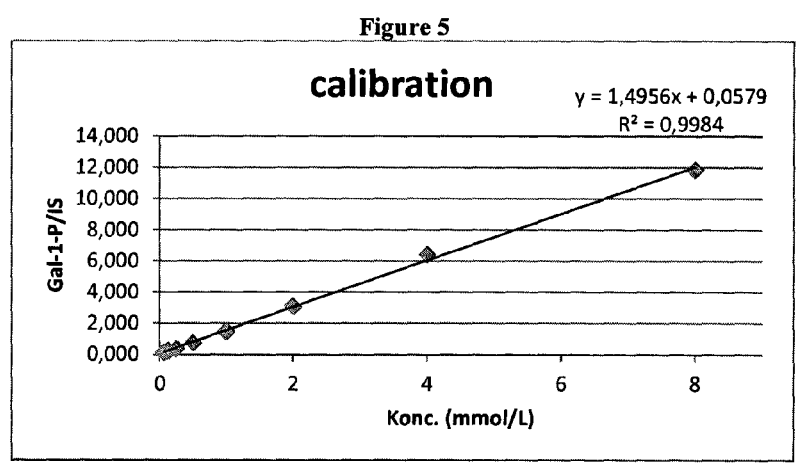

FIG. 1: The equilibrium between a straight and a ring form of simple sugars
FIG. 2: Reduction of the carbonyl group of galactose
FIG. 3: Oxidation of the carbonyl group of galactose
FIG. 4: Reactions with amines of galactose
FIG. 5: Calibration curve for GAL-1-P

EXAMPLE 1

Samples

The samples that are used are dried blood spots (DBS) on filter paper. It is also possible to use serum, plasma or full blood samples. The positive that were used use are biobanked DBS from the Danish newborn screening samples and represent all know cases of galactosemia contained in the biobank. Newborn screening samples were taken on day 6-7 until the end of year 2008. In 2009 the sampling date was changed to 48 to 72 hours after birth. Fortunately, three of the samples are recent enough to be taken at the earlier sample time (marked with an "*" in table 1). DBS from patients known to be heterozygotes for galactosemia, to be homozygotes for galactosemia and to be negative for galactosemia were analysed. DBS for negatives were both normal samples and samples from patients with other disorders.

Standard

A standard solution of GAL-1P standard containing 57.1 mmol/L GAL-1P was prepared in saline solution (0.9 g/L NaCl in water). The solution was used to prepare calibrators.

Calibrators

Blood is collected in 10 mL venoject tubes containing EDTA. The blood is cooled in order to reduce the GALT activity. 280 uL of standard is added to 1720 μL cooled blood providing a final concentration of GAL-1P of 8 mmol/L. A series of 1 to 1 dilutions is performed resulting in blood containing 4, 2, 1, 0.5, 0.25, 0.125 and 0.0625 mmol/L of GAL-1P. 75 μl of each is pipetted on to standard newborn screening filter paper. The concentration range of the calibrators was chosen to cover the range normally found in galactosemia neonates as well as found in normal neonates. The calibrators are allowed to dry overnight at room temperature. After drying the samples were stored at 4 C.

Extraction Buffer

Two different extraction buffers were prepared, one with hydrazine and one without. Both extraction buffers consisted of 80% methanol and 20% water containing 1.3 mmol/L $^{13}C_6$-Gal-1P. Other ratios of methanol-water could be used. Also, acetonitrile-water could be used as well as several other solvent systems. Concentrations ranging from 1 to 30 mmol/L can be used. As hydrazine is used as a reagent the exact concentration is not crucial, it is only important that an excess is used.

Extraction

A 3.2 mm diameter disc is punched from a DBS into a well of a microtiter plate. 100 uL of extraction buffer is added to each well. The exact amount of extraction buffer is not important, however it is crucial that the same amount of internal standard is added to each sample in a set. This is most easily insured by adding the same amount of extraction buffer to all wells. During extraction the sample is gently shaken at room temperature. After extraction the extract is transferred to a new plate. The plate is incubated at 40 to 50° C. for at least 45 minutes to allow the hydrazine reaction to take place. At this point the extract is ready for analysis. In this example all samples were punched twice in order to insure reproduceable results. One set of samples was extracted with extraction buffer with hydrazine and one set was without. This makes it possible to observe the effects of the hydrazine.

Analysis

The samples were analysed on a Water Quattro micro triple quadrupole mass spectrometer equipped with a 1525μ LC-pump and a 2777 C autosampler. The system was operated in flow injection analysis mode using an ESI ionisation probe. 30 uL of sample was injected. Any volume of extract could be injected The following transitions were monitored: 295.1/79.1 for Gal-1P and 265.1/79.1 $^{13}C_6$-Gal-1P.

Results

The calibration curve was linear across the entire concentration range are shown in FIG. 5. The average concentrations for the Gal-1P heterozygotes were 3.0 without hydrazine and 3.5 with hydrazine. The average concentrations for the Gal-1P homozygotes were 1.4 without hydrazine and 1.5 with hydrazine. The average concentrations for the Gal-1P negatives were 0.19 without hydrazine and 0.01 with hydrazine. It is quite clear that the addition of hydrazine lowers the levels of HMP in the measurements of negative samples without affecting the levels of the positives In WO0210740 the median concentration for HMP in normal samples and samples form patients with other diseases was found to be in the range of <0.10 to 0.94). Samples from galactosemia patients were found to be in the range of 2.6 to 5.2 nmol/L. These samples were also taken the Danish newborn screening biobank. However, all the samples used in WO0210740 had a sampling time of 5 to 7 days. Therefore all samples from galactosemia patients should contain steady state levels. We find that without hydrazine treatment the levels in samples from patients that are negative for galactosemia are comparable. When hydrazine treatment is used, the levels of HMP in samples from non-galactosemia patient drops dramatically and is <0.1 nmol/L. This is of major importance for one of the positive samples that was taken on day 2 to 3. Sample Y38421 has a HMP concentration of 0.59 nmol/L (0.56 nmol/L with hydrazine treatment). Without hydrazine treatment this sample would be well within the normal range and it would not be possible to distinguish it from normal samples. This would lead to a false negative if the sample was screened using tandem MS without hydrazine. In fact three sample with the later sampling date would be miss-classified as well: PK93-1820225, PK96-1900262 and PK98-1610299. They are all below 0.94 nmol/L and are therefore within the normal range for HMP when hydrazine is not used. Using hydrazine to deplete other HMP compounds than GAL-1P makes it possible to distinguish these samples as positives. It is also of interest that one of the negative samples (10DEC18R065), had an HMP concentration of 2.0 nmol/L without hydrazine treatment and would therefore be considered to well above the normal range. After hydrazine treatment this sample has an immeasurable level HMP. In this case the sample would become a false positive without hydrazine treatment but is correctly assigned as negative with hydrazine treatment.

TABLE 1

| Patient samples | Without hydrazine HMP conc. (mmol/L) | With hydrazine HMP conc. (mmol/L) | Type |
|---|---|---|---|
| PK86-980075 | 1.89 | 2.75 | Gal-1-P positive |
| PK89-1770190 | 3.17 | 3.25 | |
| PK92-1470112 | 3.53 | 3.65 | |
| PK93-1040522 | 4.44 | 5.14 | |
| PK93-1820225 | 0.64 | 0.60 | |
| PK94-1950070 | 2.92 | 3.20 | |
| PK95-3180095 | 3.82 | 5.10 | |
| PK96-1900262 | 0.83 | 0.62 | |
| PK97-1130063 | 4.30 | 5.63 | |
| PK98-1610299 | 0.49 | 0.36 | |
| PK99-9080147 | 4.13 | 5.26 | |
| PK00-9900138 | 3.23 | 2.92 | |
| Y43751 | 5.06 | 5.54 | |
| Z51831 | 2.83 | 3.34 | |
| Y48128 | 4.30 | 6.05 | |
| Y15197 | 4.80 | 5.36 | |
| Y65662 | 1.08 | 1.21 | |
| Y38421* | 0.59 | 0.56 | |
| 10FEB08R152* | 4.18 | 4.38 | |
| 10OKT06R008* | 4.64 | 5.44 | |
| Y48614 | 1.55 | 1.79 | Heterocygote Gal-1-P |
| Y55980 | 1.38 | 1.57 | |
| Y62095 | 0.96 | 1.07 | |
| Y62769 | 1.73 | 1.70 | |
| 10DEC18R065 | 2.00 | −0.01 | Negative (Positive for other diseases) |
| 10DEC29R034 | 0.04 | 0.01 | |
| 11AUG03R127 | 0.05 | 0.07 | |
| 11DEC08R096 | 0.05 | 0.01 | |
| 11DEC20R343 | 0.06 | 0.01 | |
| 12JAN03R392 | 0.04 | 0.01 | |
| 12FEB03R060 | 0.04 | 0.01 | |
| 12FEB21R096 | 0.05 | 0.00 | |
| 12FEB21R458 | 0.05 | −0.01 | Negative (negative for other diseases) |
| 12FEB21R459 | 0.05 | 0.01 | |
| 12FEB21R460 | 0.05 | 0.01 | |
| 12FEB21R461 | 0.05 | 0.01 | |
| 12FEB21R462 | 0.10 | 0.03 | |
| 12FEB21R463 | 0.08 | 0.04 | |

The invention claimed is:

1. A method of determining the galactose-1-phosphate (GAL-1-P) concentration in an early blood sample from a neonate, said blood sample comprising hexosemonophosphates including GAL-1-P and at least one hexosemonophosphate having a carbonyl group not modified in the 1 position, said method comprising oxidizing, reducing, or reacting with an amine, the carbonyl group not modified in the 1 position of said at least one hexosemonophosphate in said blood sample, such that said hexosemonophosphates not modified in the 1 position are chemically depleted, and then measuring said GAL-1-P concentration in said blood sample.

2. A method according to claim 1 where the reduction of the carbonyl group is achieved by adding borohydrate to said blood sample.

3. A method according to claim 1 where the oxidation of the carbonyl group is achieved by reacting said blood sample with nitric acid, or Tollen's or Fehling's agent.

4. A method according to claim 1 where said blood sample is reacted with a hydrazine.

5. A method according to claim 4 where the hydrazine is chosen from $N_2H_4$, monomethyl hydrazine, 1,1-dimethylhydrazine, 1,2-dimethylhydrazine, Isoniazid, iproniazid, hydralazine, phenelzine, 2,4-dinitrophenylhydrazine or phenylhydrazine.

6. A method according to claim 1 where said blood sample is collected sooner than 5 days after birth of said neonate.

7. A method according to claim 1 where the GAL-1-P concentration in said blood measured by mass-spectrometry.

8. A method of determining the galactose-1-phosphate (GAL-1-P) concentration in an early blood sample from a neonate, said blood sample comprising hexosemonophosphates including GAL-1-P and hexosemonophosphate glucose-6-phosphate (GLC-6-P), said method comprising oxidizing, reducing, or reacting with an amine, the carbonyl group not modified in the 1 position of said GLC-6-P in said blood sample, such that said hexosemonophosphates not modified in the 1 position are chemically depleted, and then measuring said GAL-1-P concentration in said blood sample.

9. A method according to claim 8 where the reduction of the carbonyl group is achieved by adding borohydrate to said blood sample.

10. A method according to claim 8 where the oxidation of the carbonyl group is achieved by reacting said blood sample with nitric acid, or Tollen's or Fehling's agent.

11. A method according to claim 8 where said blood sample is reacted with a hydrazine.

12. A method according to claim 4 where the hydrazine is chosen from $N_2H_4$, monomethyl hydrazine, 1,1-dimethylhydrazine, 1,2-dimethylhydrazine, Isoniazid, iproniazid, hydralazine, phenelzine, 2,4-dinitrophenylhydrazine or phenylhydrazine.

13. A method according to claim 8 where said blood sample is collected sooner than 5 days after birth of said neonate.

14. A method according to claim 8 where the GAL-1-P concentration in said blood sample is measured by mass-spectrometry.

15. A method of preparing an early blood sample from a neonate for analysis of galactose-1-phosphate (GAL-1-P) concentration, wherein said blood sample comprises hexosemonophosphates including GAL-1-P and at least one hexosemonophosphate having a carbonyl group not modified in the 1 position, comprising oxidizing said at least one hexosemonophosphate having a carbonyl group not modified in the 1 position, reducing said at least one hexosemonophosphate having a carbonyl group not modified in the 1 position, or reacting with an amine said at least one hexosemonophosphate having a carbonyl group not modified in the 1 position, such that said hexosemonophosphates not modified in the 1 position are chemically depleted.

16. A method according to claim 15 where the reduction of the carbonyl group is achieved by adding borohydrate to said blood sample.

17. A method according to claim 15 where the oxidation of the carbonyl group is achieved by reacting said blood sample with nitric acid, or Tollen's or Fehling's agent.

18. A method according to claim 15 where said blood sample is reacted with a hydrazine.

19. A method according to claim 18 where the hydrazine is chosen from $N_2H_4$, monomethyl hydrazine, 1,1-dimethylhydrazine, 1,2-dimethylhydrazine, Isoniazid, iproniazid, hydralazine, phenelzine, 2,4-dinitrophenylhydrazine or phenylhydrazine.

20. A method according to claim 15 wherein the GAL-1-P concentration in said blood sample is measured by mass-spectrometry.

\* \* \* \* \*